United States Patent [19]

Schlatter

[11] 4,086,220

[45] Apr. 25, 1978

[54] FRAGMENTS OF SECRETIN

[75] Inventor: James M. Schlatter, Glenview, Ill.

[73] Assignee: G. D. Searle & Co., Chicago, Ill.

[21] Appl. No.: 713,210

[22] Filed: Aug. 9, 1976

[51] Int. Cl.² .................... C07C 103/52; A61K 37/00
[52] U.S. Cl. ............................. 260/112.5 R; 424/177
[58] Field of Search ................................ 260/112.5 R

[56] References Cited

U.S. PATENT DOCUMENTS 3,812,092  5/1974  Bodansky et al. ............ 260/112.5 R

*Primary Examiner*—Delbert R. Phillips
*Attorney, Agent, or Firm*—John J. McDonnell

[57] ABSTRACT

Fragments of secretin are disclosed herein. The compounds disclosed contain the amino acid fragments of secretin having the 1–15 amino acid sequence through those having the 1–19 amino acid sequence. Also disclosed are the above secretin fragments having a protecting group on the first amino acid. The compounds are useful as gastric antisecretory agents.

8 Claims, No Drawings

FRAGMENTS OF SECRETIN

BACKGROUND OF THE INVENTION

This invention relates to amino acid fragments of secretin. Secretin is a hormone secreted by the mucosa of the duodenum and jejunum when acid chyme enters the intestine. Secretin has been isolated, and the amino acid sequence has been described as follows:

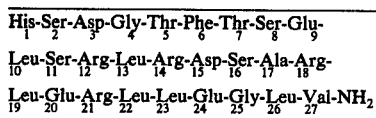

wherein the stereochemical configuration of each of the optically active amino acid residues is L.

Secretin stimulates pancreatic secretion of water and bicarbonate. In the stomach, secretin stimulates pepsin secretion, stimulates the pyloric sphincter, inhibits gastrin-stimulated acid secretion, inhibits food-stimulated gastrin release, and inhibits motility. Rayford et al, New England Journal of Medicine, May 13, 1976 (1093–2000).

SUMMARY OF THE INVENTION

The present invention is concerned with novel peptide fragments of secretin. More particularly this invention is concerned with compounds of the formula

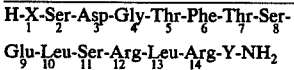

wherein
X is His or His(DNP);
Y is selected from a group consisting of
Asp,
Asp-Ser,
Asp-Ser-Ala,
Asp-Ser-Ala-Arg, and
Asp-Ser-Ala-Arg-Leu;
and the stereochemical configuration of each of the optically active amino acid residues may independently be D, L or DL.

Preferred compounds of this invention are those of formula (I) wherein X and Y are defined as hereinbefore, and all of the optically active amino acid residues are of the L-stereochemical configuration.

Also equivalent to the compounds of formula (I) for the purposes of this invention are the pharmaceutically acceptable acid addition salts thereof. Such acid addition salts can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicylic, gluconic, ascorbic and related acids.

DETAILED DESCRIPTION OF THE INVENTION

The compounds of the present invention are useful in consequence of their valuable pharmacological properties. They are useful, for example, as gastric antisecretory agents. This activity is surprising in view of statements appearing in the art, which indicate that no biological activity could be expected for any fragments of secretin. Johnson, L. R. et al., *Gastroenterology*, 60, 120–44, Jan. 71; reported "Unlike gastrin and CCK, secretin has failed to yield a portion of the molecule with biological activity. All 27 amino acids must be linked before any activity whatsoever is present".

It was also reported that "The intact secretin molecule is needed for complete biological activity. Amino acid fragments of the molecule from position 1 to 14 (containing the helical portion) possess lipolytic activity, but on a molar basis, the activity is only about 0.5 percent of that of the parent molecule". Rayform et al., supra p. 1094.

The details of the assay used to determine gastric secretory inhibition is as follows:

Adult female Beagles (5–8kg) prepared with simple Thomas type gastric fistulae are used in these experiments. The dogs were trained to stand quietly in Pavlov-type slings, while fully conscious, during all studies. The surgery was performed at least one year before the beginning of the studies, and the animals are used not more than once each week.

The compounds are dissolved in a 0.15 M saline solution and homogenized to insure uniform dispersion and particle size of any insoluble impurities. Samples are prepared fresh for each experiment.

Stock solutions of pentagastrin (1 mg/ml) in isoosmotic buffer ($Na_2HPO_4$, $NaH_2PO_4$; pH=7.4) containing pure ethyl alcohol to 20% by volume are stored at $-10°$ C. Immediately prior to each experiment, a separate pentagastrin solution in 0.15 M saline is prepared for each dog so each dog receives 4 $\mu$/kg/hr.

The dogs are fasted for 18 hours. On the morning of an experiment, the dogs are placed in Pavlov slings and infused intravenously with 0.15 M NaCl solution. Gastric secretions are collected in polyethylene bottles attached to the cannulae and measured for volume to the nearest 0.1 ml. After 15–30 min. basal secretion, the dogs are infused with the pentagastrin solution at 4 $\mu$/kg/hr. This dose was selected from previously established dose/response curves to represent 75–100% maximal secretion in this series of dogs. The volume of infusion is maintained at 6.48 ml/hr using a Harvard Compact Infusion Pump (Harvard Apparatus Company, Inc., Millis, Mass.).

Gastric juice samples are measured for total acidity by titration with 0.1 $N$ NaOH to pH 7.0 (Radiometer Automatic Titrator, Copenhagen, Denmark).

At the plateau of gastric secretion, approximately 45–60 min. after pentagastrin infusion was begun, a simultaneous infusion of the compound solution is started. This combined infusion is continued for one hour, followed by single infusion of pentagastrin to the end of the experiment.

Results are expressed in terms of percent of maximal inhibition of total acid output for the one peak interval of activity compared to each dogs' concurrent pre-dose control values. Duration is expressed as the total time (min) when total acid output was inhibited by at least 50% of the pre-dose values.

The compounds of formula (I) may be combined with various typical pharmaceutical carriers to provide compositions suitable for pharmacological use. The dosage of these compounds is dependent upon various factors, such as the particular compound employed and the particular response obtained. Typical dosages for antisecretory use vary from 1 to 1,000 μ/kg per day administered parenterally.

The manufacture of the instant novel compounds is conveniently achieved by processes adapted to the synthesis of peptides, i.e., both solution synthesis and solid-phase peptide syntheses.

The desired peptide can be obtained by solid-phase synthesis which consists of first attaching the desired C-terminal amino acid to a polystyrene resin support. A linear chain of amino acids is built through repetitive amid linkages.

The building of a linear chain of amino acids is conveniently done in an automatic peptide synthesizer. The synthesizer is programmed to carry out the systematic procedure for the addition of each amino acid. The four basic functions necessary for each amino acid addition are neutralization, addition of an N-protected amino acid, acetylation of unreacted sites, and deprotection of the amino acid.

In the case of solution syntheses, the order in which the amino acids are coupled is not critical. The desired peptide may be produced by coupling any two suitable units containing the desired amino acids.

In order to illustrate the preparation of compounds of the present invention, reference is made to the following examples, which are not intended to limit the invention in any respect. In the examples, the abbreviation BOC- is used in its accepted meaning, referring to t-butoxycarbonyl. The stereochemistry of each of the optically active amino acids in the examples is $L$ unless otherwise indicated. Temperatures are given in degrees Centigrade (° C.) and relative amounts in parts by weight, except as otherwise noted.

EXAMPLE 1

A resin of polystyrene cross linked with 1% divinyl benzene and substituted with 0.6 millimole per gram of benzylhydrylamine (10 grams) is placed in a Schwarz-Mann Model 105 automatic peptide synthesizer. The synthesizer was modified so that the agitator ran continuously. This allows the washes to agitate during the time required to fill the burette for the next wash (about 1 minute unless otherwise specified). The resin was neutralized in the following manner:

1. 20 Parts triethylamine and 140 parts methylene chloride (3 times).
2. 140 Parts methylene chloride (3 times).
3. 140 Parts isopropanol (2 times).
4. 20 Parts triethylamine and 120 parts isopropanol.
5. 140 Parts methylene chloride (7 times).

The first blocked amino acid, t-butoxycarbonyl-$L$-leucine, is added to the resin in the following manner:

6. 2.8 Parts t-butoxycarbonyl-$L$-leucine in 44 parts methylene chloride, 2.48 parts dicyclohexylcarbodiimide, in 50 parts methylene chloride, 16 hours.
7. 140 Parts 1:1 methanol-tetrahydrofuran, five minutes (2 times).
8. 140 Parts methylene chloride (3 times).
9. 140 Parts isopropanol, 2 minutes (2 times).
10. 20 Parts triethylamine and 120 parts isopropanol.
11. 140 Parts methylene chloride (7 times).

Any unreacted sites are acetylated in the following manner:

12. 140 Parts 0.3 M acetic anhydride-methylene chloride, 5 minutes.
13. 140 Parts methylene chloride (3 times).
14. 140 Parts isopropanol (2 times).
15. 20 Parts triethylamine and 120 parts isopropanol.
16. 140 Parts methylene chloride (5 times).
17. 140 Parts 0.3 M acetic anhydride-methylene chloride, 5 minutes.
18. 140 Parts methylene chloride (6 times).

The blocking group on the amino acid is removed in the following manner:

19. 140 Parts 37% trifluoroacetic acid in methylene chloride, 20 minutes.
20. 140 Parts methylene chloride (4 times).
21. 140 Parts isopropanol (3 times).
22. 140 Parts methylene chloride (6 times).
23. 140 Parts 37% trifluoroacetic acid in methylene chloride, 15 minutes.
24. 140 Parts methylene chloride (6 times).

The following amino acid residues are then introduced consecutively and each addition is treated in the manner described above by repeating the 24 steps for each addition: BOC-$N^G$-nitro-$L$-arginine (3.8 parts in 11 parts N,N-dimethylformamide and 28 parts methylene chloride); BOC-$L$-alanine (2.3 parts in 44 parts methylene chloride); BOC-$L$-serine-O-benzyl ether (3.5 parts in 44 parts methylene chloride); BOC-$L$-aspartic acid β-benzyl ester (3.9 parts in 44 parts methylene chloride); BOC-$N^G$-nitro-$L$-arginine (3.8 parts in 30 parts N,N-dimethylformamide and 14 parts methylene chloride); BOC-$L$-leucine (2.8 parts in 44 parts methylene chloride); BOC-$N^G$-nitro-$L$-arginine (3.8 parts in 30 parts N,N-dimethylformamide and 14 parts methylene chloride); BOC-$L$-serine-O-benzyl ether (3.5 parts in 44 parts methylene chloride); BOC-$L$-leucine (2.8 parts in 44 parts methylene chloride); BOC-$L$-glutamic acid γ-benzyl ester (4.1 parts in 44 parts methylene chloride); BOC-$L$-serine-O-benzyl ether (3.5 parts in 44 parts methylene chloride); BOC-$L$-threonine-O-benzyl ether (3.7 parts in 44 parts methylene chloride); BOC-$L$-phenylalanine (3.2 parts in 44 parts methylene chloride); BOC-$L$-threonine-O-benzyl ether (3.7 parts in 44 parts methylene chloride); BOC-glycine (2.1 parts in 44 parts methylene chloride); BOC-$L$-aspartic acid β-benzyl ester (3.9 parts in 44 parts methylene chloride); BOC-$L$-serine-O-benzyl ether (3.5 parts in 44 parts methylene chloride); and α-BOC-$N^{im}$-dinitrophenyl-$L$-histidine (5.1 parts in 44 parts methylene chloride). The above procedure affords the product of the formula Asp(OBzl)-Gly
3

Thr(Bzl)-Ser(Bzl)-Glu(OBzl)-Leu-Ser(Bzl)-Arg(NO$_2$)-
7    8      9         10    11     12

Leu-Arg(NO$_2$)-Asp(OBzl)-Ser(Bzl)-Ala-Arg(NO$_2$)-Leu-
13  14       15       16     17  18     19 benzylhydrylamine resin

The 1–18 amino acid fragment through the 1–15 amino acid fragments may be produced in the same manner by starting the procedure with

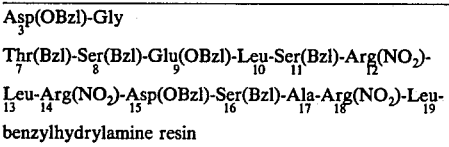

for the 1–18 fragment,

BOC-Ala
      17 for the 1-17 fragment,

BOC-Ser(Bzl)
         16 for the 1-16 fragment and

BOC-Asp(OBzl)
        15 for the 1-15 fragment and repeating the procedure from that point until the addition of all the subsequent amino acids are complete.

EXAMPLE 2

5.0 Parts of the protected peptide-resin are placed in a polyethylene reactor with a porous polyethylene bottom and drain tube. The sample is wet with 3 parts anisole and then 20 parts 9:1 liquid hydrogen fluoride-anisole is added at $-70°$ C. The mixture is stirred occasionally for 15 minutes while warming to approximately $-20$ C. The hydrogen fluoride solution is drained, and another 20 parts 9:1 hydrogen fluoride-anisole solution is added. After 15 minutes of occasional stirring the hydrogen fluoride solution is drained as before. Three more 20 part solutions of 9:1 hydrogen fluoride-anisole at $-20°$ C. is added as before.

The combined filtrates of hydrogen-fluoride are evaporated with a stream of nitrogen gas, and the residue is stirred with ether to give a solid product. The product is collected and washed with ether, then dissolved in 100 parts water. Two parts concentrated hydrochloric acid is added and the solution is stripped to dryness to remove the hydrogen fluoride. The residue is converted to the acetate form by passing an aqueous solution of the residue through a weakly basic ion exchange resin in the acetate form. The eluate is freeze dried to give the solid product.

Purification is accomplished by counter current distribution in the solvent system 2-butanol (47 parts), water (49 parts), acetic acid (1.5 parts), and pyridine (0.5 part). After 800 transfers the tubes are assayed by TLC and the tubes containing the most product are combined. After distillation of the solvents the product was dissolved in water and freeze dried. The product is represented by the formula

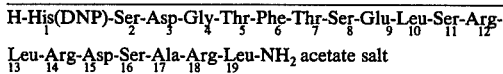 acetate salt

EXAMPLE 3

The dinitrophenyl group can be removed from histidine in the following manner. 5 Parts of the protected peptide resin of Example 1 is treated with 60 parts N,N-dimethylformamide containing 2% mercaptoethanol and 5% triethyl amine. The product is washed 3 tines with 60 parts N,N-dimethylformamide, then 3 times with 60 parts isopropanol, and then 6 times with 60 parts methylene chloride. After drying for 1 hour at 65° C. the product is treated as in Example 2 to remove the remaining protecting groups and resin.

What I claim is:

1. A compound of the formula

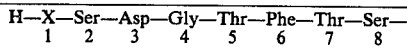
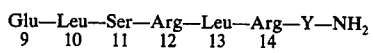

wherein
X is His or His(DNP);
Y is selected from a group consisting of
Asp,
Asp-Ser,
Asp-Ser-Ala,
Asp-Ser-Ala-Arg, and
Asp-Ser-Ala-Arg-Leu;
and the stereochemical configuration of each of the optically active amino acid residues may independently be D, L or DL.

2. A compound according to claim 1 of the formula

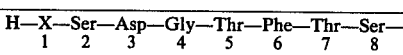
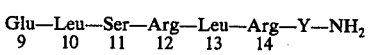

wherein
X is His or His(DNP);
Y is selected from a group consisting of
Asp,
Asp-Ser,
Asp-Ser-Ala,
Asp-Ser-Ala-Arg, and
Asp-Ser-Ala-Arg-Leu;
and the stereochemical configuration of each of the optically active amino acid residues is L.

3. A compound according to claim 1 which is L-histidyl-L-seryl-L-aspartylglycyl-L-threonyl-L-phenylalanyl L-threonyl-L-seryl-L-glutamyl-L-leucyl-L-seryl-L-arginyl-L-leucyl-L-arginyl-L-aspartyl amide.

4. A compound according to claim 1 which is L-histidyl-L-seryl-L-aspartylglycyl-L-threonyl-L-phenylalanyl L-threonyl-L-seryl-L-glutamyl-L-leucyl-L-seryl-L-arginyl-L-leucyl-L-arginyl-L-aspartyl-L-serine amide.

5. A compound according to claim 1 which is L-histidyl-L-seryl-L-aspartylglycyl-L-threonyl-L-phenylalanyl L-threonyl-L-seryl-L-glutamyl-L-leucyl-L-seryl-L-arginyl-L-leucyl-L-arginyl-L-aspartyl-L-seryl-L-alanine amide.

6. A compound according to claim 1 which is L-histidyl-L-seryl-L-aspartylglycyl-L-threonyl-L-phenylalanyl L-threonyl-L-seryl-L-glutamyl-L-leucyl-L-seryl-L-arginyl-L-leucyl-L-arginyl-L-aspartyl-L-seryl-L-alanyl-L-arginine amide.

7. A compound according to claim 1 which is L-histidyl-L-seryl-L-aspartylglycyl-L-threonyl-L-phenylalanyl L-threonyl-L-seryl-L-glutamyl-L-leucyl-L-seryl-L-arginyl-L-leucyl-L-arginyl-L-aspartyl-L-seryl-L-alanyl-L-arginyl-L-leucine amide.

8. A compound according to claim 1 which is $N^{im}$-dinitrophenyl-L-histidyl-L-seryl-L-aspartylglycyl-L-threonyl L-phenylalanyl-L-threonyl-L-seryl-L-glutamyl-L-leucyl-L-seryl-L-arginyl-L-leucyl-L-arginyl-L-aspartyl-L-seryl-L-alanyl-L-arginyl-L-leucine amide.

* * * * *